(12) United States Patent
Pierce, Jr. et al.

(10) Patent No.: US 8,599,382 B2
(45) Date of Patent: Dec. 3, 2013

(54) AUTOMATED IN SITU CONTAMINANT DETECTION SYSTEM

(75) Inventors: Richard H. Pierce, Jr., Sarasota, FL (US); Gary J. Kirkpatrick, Sarasota, FL (US); Alan R. Hails, Osprey, FL (US); Michael S. Henry, Bradenton, FL (US)

(73) Assignee: Mote Marine Laboratory, Sarasota, FL (US)

( * ) Notice: Subject to any disclaimer, the term of this patent is extended or adjusted under 35 U.S.C. 154(b) by 0 days.

(21) Appl. No.: 13/276,487

(22) Filed: Oct. 19, 2011

(65) Prior Publication Data

US 2012/0105830 A1 May 3, 2012

Related U.S. Application Data

(60) Provisional application No. 61/405,409, filed on Oct. 21, 2010.

(51) Int. Cl.
*G01N 21/00* (2006.01)

(52) U.S. Cl.
USPC ........ 356/436; 250/343; 250/252.1; 356/317; 356/435; 356/334

(58) Field of Classification Search
USPC .......... 356/436, 317, 334–343, 435; 250/343, 250/343.1, 343.3, 252.1
See application file for complete search history.

(56) References Cited

U.S. PATENT DOCUMENTS

| | | | | |
|---|---|---|---|---|
| 5,204,525 A | * | 4/1993 | Hillman et al. | 250/252.1 |
| 5,931,779 A | * | 8/1999 | Arakaki et al. | 600/310 |
| 6,727,498 B2 | * | 4/2004 | Fries et al. | 250/288 |

* cited by examiner

*Primary Examiner* — Gregory J Toatley
*Assistant Examiner* — Iyabo S Alli
(74) *Attorney, Agent, or Firm* — Foley Hoag LLP

(57) ABSTRACT

The present invention provides methods and apparatuses for in situ chemical analysis of liquid sample for the collection, identification, and measurement of chemical moieties, such as, biotoxins, organic compounds, or chemical contaminants, in aquatic environments. The apparatuses of the present invention relate to an automated in situ sampler for chemical stressors that adversely impact biological systems in aquatic environments. The apparatuses of the present invention are designed as a means to automatically collect liquid (e.g., water) samples and analyze them for the presence of chemical moieties. The apparatuses of the present invention are designed to automatically collect multiple liquid samples, extract and separate chemical moieties contained within the samples, and analyze the chemical moieties to determine the composition and concentration of the chemical moieties over time and space. The apparatuses of the present invention can be used for in situ sample collection and analysis in all weather conditions safely and economically without the need for vessels or human involvement.

7 Claims, 2 Drawing Sheets

AUTOMATED IN SITU CONTAMINANT DETECTION SYSTEM

CROSS-REFERENCE TO RELATED APPLICATIONS

This application claims the benefit of priority to U.S. Provisional Application No. 61/405,409, filed on Oct. 21, 2010, the entire contents of which are expressly incorporated herein by reference.

FIELD OF INVENTION

The present invention relates to the detection, identification, and measurement of chemical moieties, such as organic compounds, in an aqueous medium or environment. The present invention also relates to portable apparatuses and methods for performing in situ chemical analyses of aqueous environments, such as for performing chemical analysis of organic compounds and biotoxins.

BACKGROUND OF INVENTION

Blooms of the toxic dinoflagellate, *Karenia brevis*, are a frequent occurrence off the coast of Florida. Harmful algal blooms pose a threat and efforts to reduce or eliminate their negative impacts and consequences are necessary. In the Gulf of Mexico, toxic blooms of *K. brevis* regularly lead to untimely restrictions on commercial and recreational shellfish harvesting and deleterious effects on tourism and public health. Toxic blooms of *K. brevis* are generally detected by visual confirmation (e.g., water discoloration and fish kills), illness to shellfish consumers, or human respiratory irritation with actual toxicity verified through time-consuming chemical analyses for brevetoxins within shellfish samples and mouse bioassays. Currently, biological monitoring programs primarily rely on microscope-based cell enumeration and gross measurements of a biochemical parameter, such as chlorophyll-a concentration. Existing methods can be slow, labor intensive, intermittent, and do not always provide timely or accurate measurements. Existing methods also do not provide estimates of toxin in water, only of organisms that produce biotoxins. The portable apparatuses of the present invention provide for quantitation of biotoxins in aqueous environments.

Measuring chemical moieties, such as organic compounds, in aquatic environments is necessary for environmental monitoring, identifying usage patterns of pollutants, and determining levels, transport and fate of the organic compounds and potential pollutants in aquatic environments. The most widely accepted technique for carrying out this monitoring is a combination of spot sampling followed by laboratory-based extraction and determination of chemical moieties of interest. This technique, however, yields only discrete time measurements of chemical contaminants. Increasing sampling frequency may improve this limitation and provide a more accurate picture of time-integrated pollutant levels, although it can be cost prohibitive. The present invention provides an economical and effective means to assess chemical moieties over time and space via mounting an automated chemical analysis apparatus onto autonomous underwater vehicles. Remotely operative vehicles (ROVs) and autonomous underwater vehicles (AUVs) offer a means for analyzing water components in situ in harsh underwater environments.

REVIEW OF PRIOR ART

Kirkpatrick et al. (U.S. Pat. No. 7,235,248) describe an Optical Phytoplankton Discriminator (OPD) detector for detecting the presence of toxin-producing organisms based on spectral characteristics of algal species according to chlorophyll absorbance pattern analysis. The OPD described by Kirkpatrick et al. lacks a means to extract, process, and/or separate water to be analyzed at a chemical level through, for example, the use of solid phase adsorption and/or chromatographic methods.

Fries et al. (U.S. Pat. No. 6,727,498) describe a portable mass spectrometer for underwater use that includes a water-tight case having an inlet and means for transforming an analyte gas molecule from a solution phase into a gas phase within the case. The case also houses a means for directing a fluid to the transforming means from the inlet and a means for analyzing the gas-phase analyte molecule to determine its identity. However, the described detector for small, gas molecules is not applicable to detecting biotoxins, polyaromatic hydrocarbons (PAHs), or any of the industrial contaminants that can be detected by the detector of the present invention.

Hill et al. (U.S. Pat. No. 7,591,979) describe an automated self-contained device for detecting toxic agents in a water supply that includes an analyzer for detecting toxic agents in a water sample. This detector is based on fluorometric analysis of chlorophyll. The device described by Hill et al. lacks a means to extract, process, and/or separate water to be analyzed at a chemical level through, for example, the use of solid phase adsorption and/or chromatographic methods.

Petty et al. (2004) *Chemosphere* 54:695-705 describe a passive integrative sampling device that can be used to determine the presence of a broad array of contaminants. The device uses a semipermeable membrane to sample contaminants, including organochlorine pesticides, polycyclic aromatic hydrocarbons, organophosphate pesticides, and pharmaceutical chemicals. The collection technology of Petty et al. differs from that of the present invention and does not include in situ detection. The apparatuses described by Petty et al. collects water samples and analyzes such water samples without concentrating or separating chemical moieties within the samples onto adsorption column. The apparatuses of the present invention can concentrate chemical contaminants from water by passing water through a solid phase adsorption column. The mix of chemical moieties collected on the column can then be separated by eluting them via a solvent streamed through the column and analyzing individual chemical moieties as they pass through a spectrophotometric detector.

Namieśnik et al. (2005) *Anal. Bioanal. Chem.* 381:279-301 describe passive samplers filled with sorbent, such as granular activated carbon, to determine trace organic contaminants. Other investigators have described a time-integrated sampler for organic pollutants which collects compounds by accumulation in a dosimeter packed with C18-coated solid phase, or other resins, to measure PAHs or other contaminants in aquatic environments (see, Grathwohl and Schiedek (1997) *Proc. 1st Intl. Conf Strat. Tech. Invest. Monit. Contaminated Sites*, J. Gottlieb, H. Hotzl, K. Huck, R. Niessner, eds. Kluwer Academic Publishers, pp. 33-36). Such passive samplers lack a means to extract, process, and/or separate liquid (e.g., water) samples to be analyzed.

Kingston et al. (2000) *J. Environ. Monit.* 2:487-495 and Kingston et al. (U.S. Pat. No. 7,059,206) describe a sampling system for measurement of time-averaged concentration of organic micropollutants in aquatic environments. This system is an aquatic passive sampling device comprising a diffusion-limiting membrane and a receiving phase comprising an immobilized solid phase material supported by a solid support. The sampling strategy is based on diffusion of targeted organic compounds through the rate-limiting membrane, which accumulates a wide range of analytes in the bound, hydrophobic, solid-phase material. Accumulation rates are regulated by selection of diffusion-limiting membrane and bound solid-phase materials and are dependent on physico-chemical properties of individual target analytes. The solid support and membrane features enable the device to be adapted for use for continuously monitoring a variety of micropollutants, including polar organic, non-polar organic, and inorganic analytes.

Solid phase microextraction (SPME), a combination of passive and dynamic methods, has also been described to measure contaminants in water. SPME fiber can be used to extract target analytes directly in the field. In this design, analytic sampling is based on transport to and adsorption in a thin film of stationary phase coated on an SPME fiber of a stainless-steel capillary with a modified inner surface. Analytes are concentrated on the surface of the stationary phase and then are transferred to a gas or liquid chromatograph. This type of sampling is not suitable for long-term monitoring and results are comparable to those obtained via grab sampling.

Utvik et al. (1999) *Marine Pollution Bulletin* 38:977-989 describe sampling techniques for PAH in seawater via solid-phase extraction using polystyrene-divinylbenzene disks. This sampler uses different technology than that described in the present invention. This sampler does not include the in situ separation and detector system described for the present invention.

An ROV-based submersible gas chromatograph-mass spectrometer (GCMS) system with automated membrane introduction was described in an article by G. Matz et al. (1999) *J. Chromatogr. A* 830:365-376. The submersible GCMS system uses a large ion pump and is a significantly larger instrument than the portable and transportable apparatuses of the present invention.

SUMMARY OF INVENTION

The present invention provides an automated in situ sampler for the collection, identification, and measurement of chemical moieties (e.g., compounds, biotoxins, organic molecules, or other chemical contaminants indicative of aquatic stress) in aquatic environments. The apparatuses of the present invention relate to an automated in situ sampler for chemical stressors that adversely impact biological systems in aquatic environments. The apparatuses of the present invention are designed as a means to automatically collect liquid (e.g., water) samples and analyze them for the presence of chemical moieties. The apparatuses of the present invention are designed to automatically collect multiple liquid samples, extract and separate chemical moieties contained within the samples, and analyze the chemical moieties to determine the composition and concentration of the chemical moieties over time and space. The apparatuses of the present invention can be used for in situ sample collection and analysis in all weather conditions safely and economically without the need for vessels or human involvement.

The apparatuses of the present invention are designed to be used for automated collection of liquid (e.g., water) samples from aquatic environments that potentially contain chemical moieties, such as organic stressors and organic chemical compounds. In one embodiment, the apparatuses of the present invention specifically target chemical moieties that can be collected from the liquid (e.g., water) sample by solid phase adsorption and separated from other components in the sample. In some embodiments, biotoxins are desired to be detected. Such biotoxins include brevetoxins, which comprise a suite of polyketide secondary metabolites, which are part of a larger family of dinoflagellate-derived polyketide toxins that pose a threat to human health. Brevetoxins are polyether ladder type compounds having two parent backbone structures, brevetoxin A and brevetoxin B, each with several side-chain variants. Examples of other polyketide toxins of interest include ciguatoxin, okadaic acid, and the related kinophysistoxins, pectenotoxins, yessotoxin, and the azaspiracids. In other embodiments, environmental pollutants are desired to be detected and include polychlorinated biphenyls (PCBs); pharmaceuticals; DDT and its metabolites; organic compounds found in the sea environment and identified as potentially harmful and/or toxic; polychlorinated triphenyls (PCTs); dibenzo-dioxins (PCDDs); dibenzo-furans (PCDFs); chlorophenols; hexachlorocyclohexanes (HCHs); toxaphenes; dioxins; brominated flame retardants; polyaromatic hydrocarbons (PAHs); and polybrominated diphenyl ethers (PBDEs). Chemical moieties within the samples can be identified through UV or visible light spectrophotometry and comparison of spectra against those of known chemical moieties.

When mounted in a watertight housing on an autonomous underwater vehicle (AUV), the apparatuses of the present invention can automatically collect liquid (e.g., water) samples from an aqueous environment and subsequently analyze the samples for the presence of chemical moieties. Automatic water collection can be achieved by pumping water in through an inlet and flow controls valves can be used to sequentially deliver individual chemical moieties to a detector system for analysis.

DETAILED DESCRIPTION OF INVENTION

The apparatuses of the present invention are designed for extended use underwater and are designed to be mounted on an autonomous underwater vehicle. The apparatuses of the present invention are designed to collect periodic in situ aliquots of water over time. The apparatuses of the present invention include a means for collection of liquid (e.g., water) samples, a means for separating chemical moieties within the sample into individual chemical moieties; and a means, such as flow control valves, to deliver individual chemical moieties to a detector system. The apparatuses of the present invention require a watertight enclosure and a pumping system for liquid sample intake and discharge of processed liquid samples. A device comprising watertight enclosures and pumping systems is described in Kirkpatrick et al. (U.S. Pat. No. 7,235,248), which is hereby incorporated in its entirety herein by this reference.

In one embodiment, the apparatuses of the present invention contain a portable and mobile solid-liquid chromatograph that collects chemical moieties from the liquid samples to be assayed. In the solid phase collection process, desired chemical moieties are collected via adsorption onto any solid surface suitable for extracting the desired chemical moieties to be collected (e.g., having the desired adsorption selectivity, sensitivity, linearity, efficiency, capacity, and/or solvent elution recovery properties). For example, hydrophobic, bonded surfaces, such as those presenting C-18 bonded alkyl groups, can be used to collect biotoxins based on their hydrophobic properties. The adsorption medium can include minute particles and/or comprise well known media, such as silica, ion exchange polymers, size exclusion polymers, and the like. The particles can include a bonded surface that interacts with the various chemical moieties to facilitate separation of the desired chemical moieties. One suitable bonded surface is a hydrophobic-bonded surface, such as an alkyl-bonded, a cyano-bonded, or a pentafluorophenylpropyl (F5) surface.

Alkyl-bonded surfaces may include, for example, C-4, C-8, C-12, C-18 or other known bonded alkyl groups. In some embodiments, C-18 bonded solid phase extraction media is used.

Collected chemical moieties are then separated and transported, using a mobile phase solvent, to an analytical column, e.g., high pressure liquid chromatography (HPLC), for identification. Generally, liquid chromatography methods, including HPLC, rely on laminar flow technology. HPLC analyses typically rely on column packing in which laminar flow of the sample through the column is the basis for separation of the analyte of interest from the sample. The skilled artisan will understand that separation in such columns is a diffusional process and can select HPLC instruments and columns that are suitable for use with extracting the desired chemical moieties to be detected. The chromatographic column typically includes a medium (e.g., a packing material) to facilitate separation of chemical moieties (i.e., fractionation). The medium can include minute particles and/or comprise well known media, such as silica, ion exchange polymers, size exclusion polymers, and the like. The particles can include a bonded surface that interacts with the various chemical moieties to facilitate separation of the chemical moieties. One suitable bonded surface is a hydrophobic bonded surface such as an alkyl bonded, a cyano bonded, or a pentalluorophenylpropyl (F5) surface. Alkyl bonded surfaces may include, for example, C-4, C-8, C-12, C-18 or other known bonded alkyl groups. In some embodiments, C-18 bonded solid phase extraction media can be used. In other embodiments, XAD resin, Teflon® strips, polyethylene strips, or any number of well-known liquid chromatography columns having the desired adsorption properties can be used. The chromatographic column includes an inlet port for receiving a sample directly or indirectly from an extraction column, such as a solid-phase extractor, and an outlet port for discharging an effluent that includes the fractionated sample.

Once fractionated, the chemical moieties to be detected can be transported for detection using solvent elution. In one embodiment, the detection step can be accomplished using a liquid waveguide capillary cell (LWCC) that measures the concentration of detected chemical moieties using spectrophotometry. An LWCC is a flow cell capable of measuring absorbance in the ultraviolet (UV), visible, and/or near infrared light ranges. Samples containing chemical moieties to be detected can be introduced into an LWCC via an inlet and light of the desired spectrum can be passed through the sample in the LWCC (e.g., through a fiber optic cable) and directed toward a detector. In one embodiment, a uv-vis spectrophotometric detector system can be used, such as a system that uses a deuterium-tungsten light source. For example, the ultraviolet mode of the uv-vis detector system can be used to identify toxic organic moieties, such as brevetoxins, In other embodiments, tandem mass spectrometry (MS/MS)-, fluorescence-, or other well-known chemical detection formats can be used to detect chemical moieties. Spectral absorbance measurements can be made using a suitable detection device, such as a charged coupled device (CCD).

Thus, the collection and analytical chromatography steps provide for comparing the spectral patterns of known chemical moieties against those produced from the chemical moieties within the analyzed sample according to the appropriate retention window characteristic of the desired chemical moieties to be identified. The apparatuses of the present invention can further be calibrated periodically using standard solutions containing chemical moieties of known qualitative and quantitative parameters. Such calibration allows for the definition of spectrophotometric standard curves for individual chemical moieties at specific light wavelengths and concentrations, which can provide additional precision to the identification of chemical moieties.

Once detected, the qualitative and quantitative data obtained in situ can be processed locally or, alternatively, sent remotely to a data analysis station. Such remote data transmission can be achieved using any number of known methods, including satellite communication, radio communication, Internet communication, wireless communication, and telephone communication methods. Whether the data is processed locally or remotely, the apparatuses of the present invention provide for continuous, near real-time processing and dissemination of the data. In addition, the pumping systems described herein provide for the automatic reconditioning of apparatuses components (e.g., solid-phase adsorption collectors) in preparation for analysis of subsequent in situ liquid (e.g., water) samples.

BRIEF DESCRIPTION OF THE DRAWINGS

The present invention can be better understood by way of the specific embodiments shown in the following figures, the purpose of which is to illustrate the invention rather than to limit its scope.

DETAILED DESCRIPTION OF THE DRAWINGS

Figure 1:
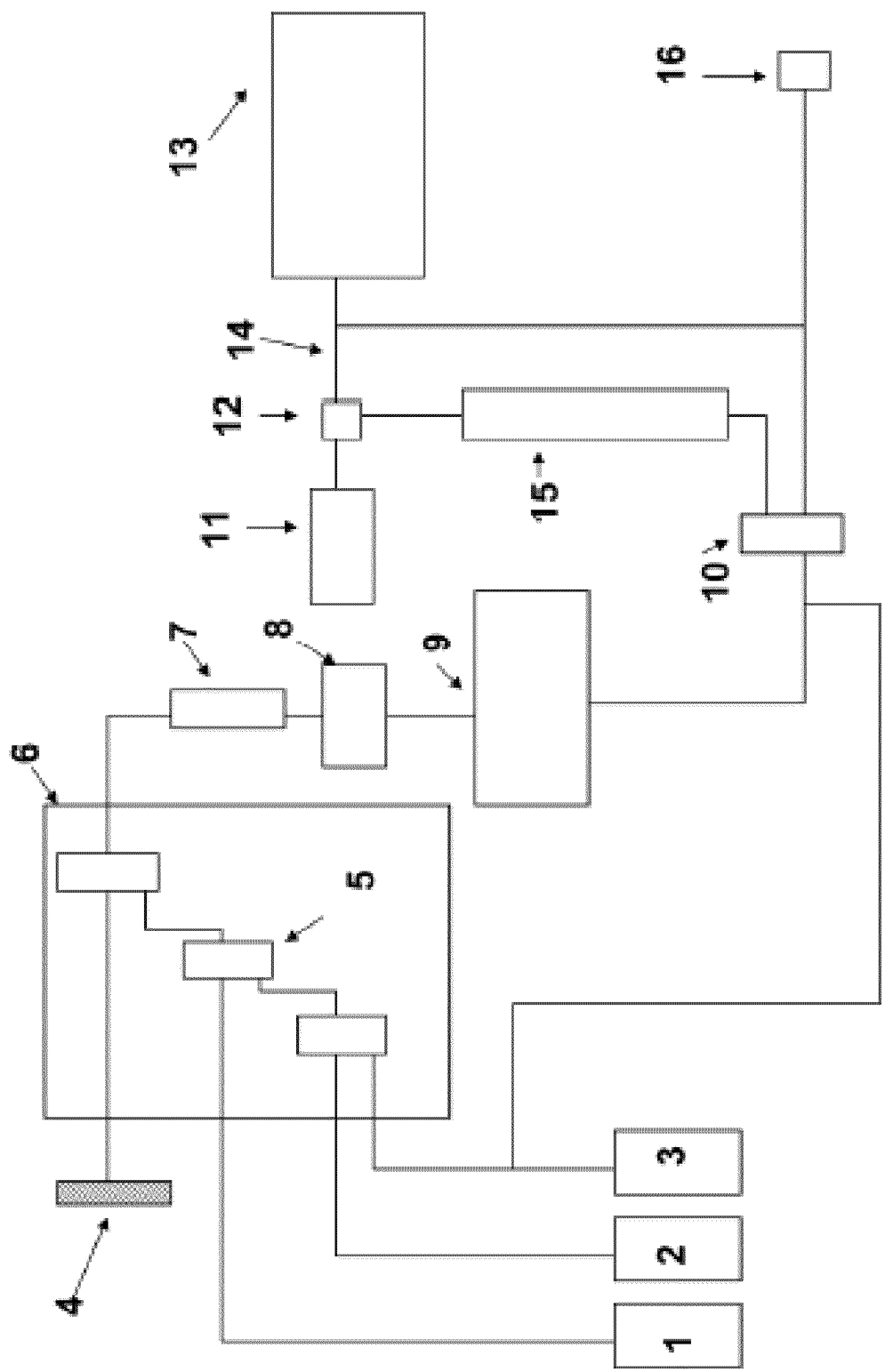
FIG. 1 is a flow system schematic for chemical stressor collection on adsorption column, separation on chromatography column, and delivery to a UV spectrophotometer.
Figure 2:
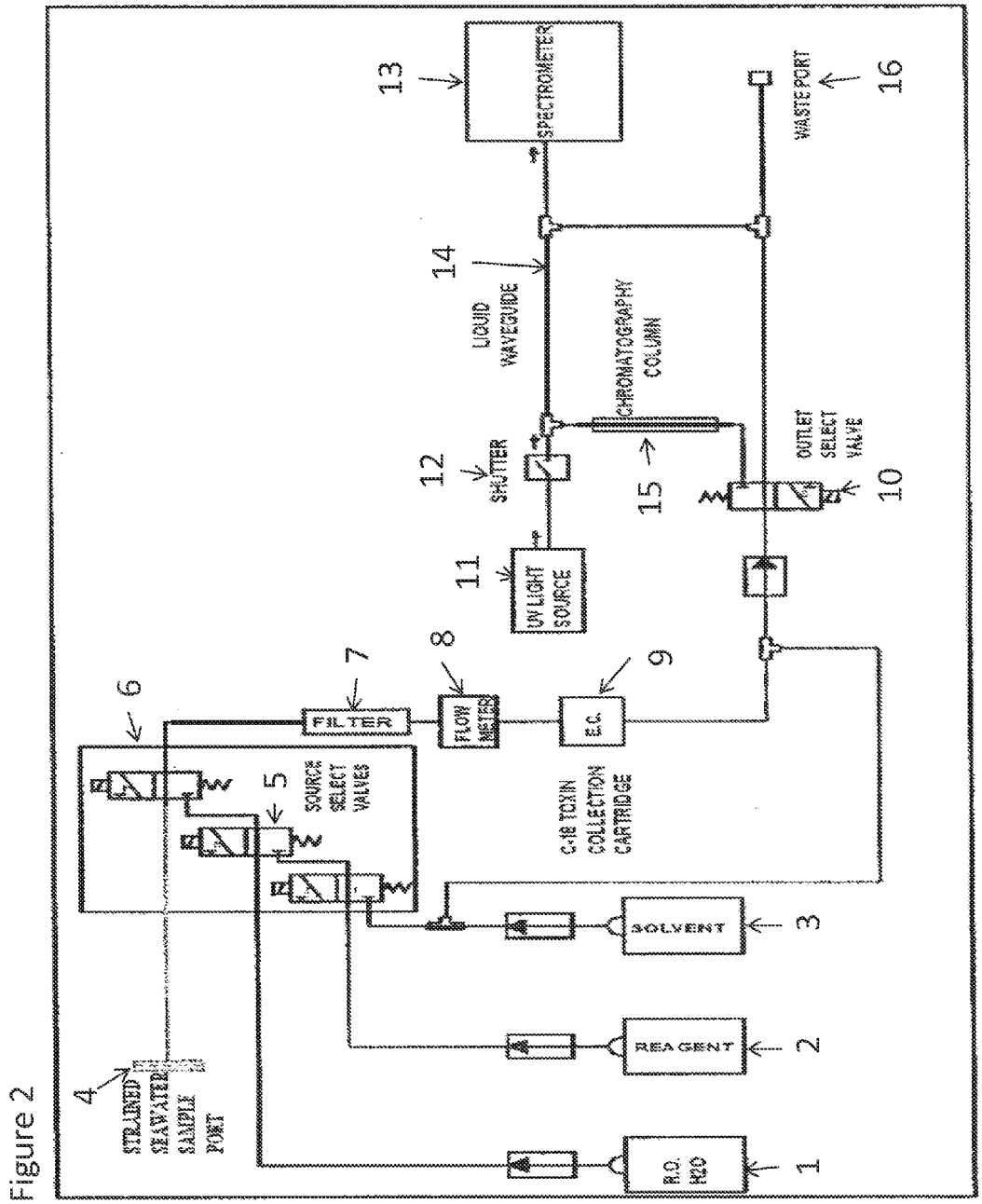
FIG. 2 is a depiction of the flow system described in FIG. 1 with detailed structural features.

Methanol (3) can flow in a reverse direction through the C-18 pre-column extraction module (9) to condition the C-18 column and remove any contaminants from previous samples. This solution can be discharged through a waste port (16). Reverse osmosis water (1) can be passed through a C-18 extraction module (9) in the forward direction and discharged through a waste port (16) to remove methanol and prepare for the extraction. Seawater sample can be pumped in through a seawater sample port (4) and directed through a C-18 extraction module (9) to collect chemical moieties. Extracted seawater can be discharged through a waste port (16). The C-18 extraction module (9) is rinsed with reverse osmosis water (1) to remove salts and to lyse cells, if present, by osmotic shock which releases intracellular toxin to the C-18 extraction module (9). A valve system (6) can be switched to allow a solution of 70% methanol (2) to be passed through the C-18 extraction module (9) to the analytical column (14) where the extract can be separated into individual chemical moieties (e.g., through HPLC) prior to entering the liquid waveguide detector system (14). UV light (11) can be passed through the waveguide detector system (14) to the spectrophotometer (13) to create individual spectra for each compound. Individual spectra can be collected only during the proper retention time window predetermined for each compound. The C-18 extraction module (9) can be cleaned and reconditioned by back-flushing with 100% methanol (3) to prepare for the next sample. The apparatuses can be calibrated periodically with a reservoir containing compound standards for periodic qualitative and quantitative verification.

IDENTIFICATION NUMBERS ON DRAWING

1. Reverse osmosis water
2. 70% methanol
3. 100% methanol
4. seawater sample port with strainer
5. source select valves
6. housing for source select valves
7. filter
8. flow meter
9. C-18 extraction module 10. outlet select valve
11. UV light source
12. shutter
13. spectrometer
14. liquid waveguide
15. chromatography column
16. waste port

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An apparatus for analyzing liquid samples, the apparatus comprising:
    a) bidirectional ports for providing liquid samples to the apparatus and discharging liquid samples from the apparatus;
    b) means for solid phase extraction of liquid samples;
    c) a liquid waveguide capillary cell in fluid communication with the bidirectional ports and arranged to analyze different liquid samples at the same time;
    d) at least one light source, at least one shutter, and at least one spectrophotometer in optical communication with the liquid waveguide capillary cell; and
    e) a bidirectional pump or control arranged to flow samples in alternate direction through the bidirectional ports.

2. An apparatus of claim 1 capable of roving analysis in an autonomous underwater vehicle.

3. An apparatus of claim 1 which targets chemical moieties for removal from water by solid phase extraction.

4. An apparatus of claim 1 capable of continuous monitoring over time.

5. The apparatus of claim 1 which targets chemical moieties for separate ion using solid-liquid chromatography.

6. A method for analyzing liquid samples comprising:
    a) obtaining one or more liquid samples through a first bidirectional port;
    b) flowing sample(s) into a liquid waveguide capillary cell;
    c) analyzing contents of said liquid waveguide capillary cell by spectrophotometric means;
    (d) creating and collecting spectra of said contents; and
    (e) discharging samples through a second bidirectional port.

7. A method according to claim 6, wherein samples are obtained by roving underwater analysis through a bed of varying analyte.

* * * * *